(12) United States Patent
Choi et al.

(10) Patent No.: US 10,251,615 B2
(45) Date of Patent: Apr. 9, 2019

(54) X-RAY IMAGING DEVICE

(71) Applicants: Vatech Co., Ltd., Gyeonggi-do (KR); Vatech Ewoo Holdings Co., Ltd., Gyeonggi-do (KR)

(72) Inventors: Sung Il Choi, Gyeonggi-do (KR); Tae Woo Kim, Gyeonggi-do (KR); Tae Ki Hong, Gyeonggi-do (KR)

(73) Assignees: VATECH Co., Ltd., Gyeonggi-do (KR); VATECH EWOO Holdings Co., Ltd., Gyeonggi-do (KR)

( * ) Notice: Subject to any disclaimer, the term of this patent is extended or adjusted under 35 U.S.C. 154(b) by 248 days.

(21) Appl. No.: 14/913,440

(22) PCT Filed: Aug. 20, 2014

(86) PCT No.: PCT/KR2014/007739
§ 371 (c)(1),
(2) Date: Feb. 22, 2016

(87) PCT Pub. No.: WO2015/026163
PCT Pub. Date: Feb. 26, 2015

(65) Prior Publication Data
US 2016/0199012 A1 Jul. 14, 2016

(30) Foreign Application Priority Data
Aug. 20, 2013 (KR) .................. 10-2013-0098642

(51) Int. Cl.
*A61B 6/14* (2006.01)
*A61B 6/00* (2006.01)
(Continued)

(52) U.S. Cl.
CPC ............ *A61B 6/4452* (2013.01); *A61B 6/032* (2013.01); *A61B 6/14* (2013.01); *A61B 6/4441* (2013.01);
(Continued)

(58) Field of Classification Search
CPC ........... A61B 6/032; A61B 6/035; A61B 6/14; A61B 6/4441; A61B 6/4452; A61B 6/463;
(Continued)

(56) References Cited

U.S. PATENT DOCUMENTS 4,340,971 A * 7/1982 Furuichi .................. H02P 5/50
378/40
5,305,368 A 4/1994 Bisek et al.
(Continued)

FOREIGN PATENT DOCUMENTS

CN 102711622 A 10/2012
EP 1491145 A1 12/2004
(Continued)

OTHER PUBLICATIONS

European Patent Office, Supplementary European Search Report of EP Patent Application No. 14837639.5, dated Mar. 24, 2017.
(Continued)

*Primary Examiner* — Irakli Kiknadze
(74) *Attorney, Agent, or Firm* — IP Legal Services, LLC

(57) ABSTRACT

Disclosed is an X-ray imaging device, the device including: an X-ray radiation unit for radiating X-rays to the predetermined target areas of an object to be imaged in respective imaging positions; an X-ray sensing unit for receiving the X-rays; a movement unit for arranging the X-ray radiation unit and the X-ray sensing unit to allow the X-ray radiation unit and the X-ray sensing unit to face each other in the respective imaging positions, with the object located therebetween; a position information provision unit for providing position information of the X-ray radiation unit and the X-ray sensing unit, position information of the variable rotary shaft, and position information of the target areas; a control unit for controlling the X-ray radiation unit, the
(Continued)

X-ray sensing unit, and the movement unit; and an image processing unit for producing three-dimensional images of the object from the projection data.

9 Claims, 8 Drawing Sheets

(51) Int. Cl.
    *G06T 7/00*         (2017.01)
    *G06T 15/00*       (2011.01)
    *G06T 15/08*       (2011.01)
    *A61B 6/03*        (2006.01)

(52) U.S. Cl.
    CPC ............ *A61B 6/466* (2013.01); *A61B 6/5205* (2013.01); *G06T 7/0012* (2013.01); *G06T 15/005* (2013.01); *G06T 15/08* (2013.01); *A61B 6/035* (2013.01); *A61B 6/463* (2013.01); *G06T 2200/04* (2013.01); *G06T 2207/10116* (2013.01); *G06T 2207/30036* (2013.01)

(58) Field of Classification Search
    CPC ....... A61B 6/466; A61B 6/5205; A61B 6/469; A61B 6/06; A61B 6/4233; A61B 6/025; A61B 6/501; A61B 6/037; A61B 6/04; A61B 6/0457; A61B 6/0478; A61B 6/145; A61B 6/5223; A61B 6/548; A61B 1/07; A61B 5/0042; A61B 5/0084; A61B 5/6852; G06T 15/005; G06T 15/08; G06T 2200/04; G06T 2207/10116; G06T 2207/30036; G06T 7/0012; G06T 11/006; G06T 2207/10081; G06T 2207/30004; G06T 2210/41; G06T 2207/30; G06K 9/00221; G06K 9/2027; G06K 9/3233; G06K 9/3241; G06K 2009/2045; G06K 2209/05; G06K 2209/40; G06K 9/00362; G06K 9/34; A01K 29/00; G01B 11/022; G08B 13/19602; G08B 13/19634; G08B 13/1963; G08B 13/19652; H04B 7/26; H04N 5/782; H04N 5/765; H04N 5/77; H04N 5/7822; H04N 5/9201; H04N 5/9205; H04N 5/78263; G01G 13/24; G01G 23/3735
    USPC ......................................... 378/19, 38–40, 62
    See application file for complete search history.

(56) References Cited

U.S. PATENT DOCUMENTS

| | | |
|---|---|---|
| 5,355,398 A | 10/1994 | Nakano et al. |
| 6,018,563 A | 1/2000 | Arai et al. |
| 7,787,586 B2 | 8/2010 | Yoshimura et al. |
| 2001/0036246 A1 | 11/2001 | Graumann |
| 2003/0235265 A1 | 12/2003 | Clinthorne et al. |
| 2004/0066877 A1 | 4/2004 | Arai et al. |
| 2005/0117693 A1 | 6/2005 | Miyano |
| 2005/0117696 A1 | 6/2005 | Suzuki et al. |
| 2006/0067464 A1 | 3/2006 | Clinthorne et al. |
| 2006/0203959 A1 | 9/2006 | Spartiotis et al. |
| 2008/0118024 A1 | 5/2008 | Cho et al. |
| 2009/0310845 A1 | 12/2009 | Ogawa et al. |
| 2010/0054403 A1 | 3/2010 | Ro et al. |
| 2010/0246755 A1* | 9/2010 | Suzuki ................... A61B 6/032 378/11 |
| 2012/0020450 A1 | 1/2012 | Jung et al. |
| 2012/0025088 A1 | 2/2012 | Nakayama |
| 2012/0307960 A1 | 12/2012 | Choi, II et al. |
| 2012/0314835 A1 | 12/2012 | Mueller |
| 2013/0114799 A1 | 5/2013 | Yamakawa et al. |
| 2013/0177213 A1 | 7/2013 | Lee et al. |
| 2015/0305696 A1 | 10/2015 | Yamakawa et al. |

FOREIGN PATENT DOCUMENTS

| | | |
|---|---|---|
| JP | 10-052423 A | 2/1998 |
| JP | 2006-325978 A | 12/2006 |
| JP | 2010-046360 A | 3/2010 |
| JP | 2012-024516 A | 2/2012 |
| JP | 2013-135765 A | 7/2013 |
| KR | 10-2006-0085310 A | 7/2006 |
| KR | 10-2008-0054702 A | 6/2008 |
| KR | 10-2009-0113494 A | 11/2009 |
| KR | 10-2010-0070160 A | 6/2010 |
| KR | 10-2010-0070817 A | 6/2010 |
| KR | 10-2010-0070822 A | 6/2010 |
| KR | 10-2011-0083153 A | 7/2011 |
| KR | 10-2012-0010639 A | 2/2012 |
| KR | 10-2013-0018896 A | 2/2013 |
| KR | 10-2013-0081798 A | 7/2013 |
| WO | 2012/008492 A1 | 1/2012 |

OTHER PUBLICATIONS

European Patent Office, European Search Opinion of EP Patent Application No. 14837639.5, dated Mar. 24, 2017.

European Patent Office, Supplementary European Search Report of EP Patent Application No. 14838466.2, dated Mar. 24, 2017.

European Patent Office, European Search Opinion of EP Patent Application No. 14838466.2, dated Mar. 24, 2017.

* cited by examiner

X-RAY IMAGING DEVICE

CROSS REFERENCE TO RELATED APPLICATIONS

This application is a National Stage Patent Application of PCT International Patent Application No. PCT/KR2014/007739 (filed on Aug. 20, 2014) under 35 U.S.C. § 371, which claims priority to Korean Patent Application No. 10-2013-0098642 (filed on Aug. 20, 2013), the teachings of which are incorporated herein in their entireties by reference.

TECHNICAL FIELD

The present invention generally relates to an X-ray imaging device. More particularly, the present invention relates to an X-ray imaging device in which a three-dimensional image can be produced by using a detector having a small width.

BACKGROUND ART

In general, X-rays radiated to an object to be imaged are attenuated depending on an X-ray attenuation coefficient of a substance located on a radiating path by photoelectric effect or Compton scattering. X-ray imaging is a radiation photographing method using a penetration characteristic of X-rays, and image information of an internal structure of the object is provided based on the amount of accumulated attenuation in a process of penetrating through the object. Generally, an X-ray imaging device includes an X-ray source radiating the X-rays, an X-ray detector detecting the X-rays penetrating through the object while allowing the X-ray detector and the X-ray source to face each other with the object located therebetween, and an image processing unit forming an X-ray image by using a detection result of the X-ray detector.

The penetration image showing overlapped the internal structures in a direction of the X-rays radiated to the object is obtained, and a three-dimensional image of the object may be obtained by applying image processing, such as volume rendering and/or surface rendering, to multidirectional X-ray images for the object. A variety of tomograms may be obtained depending on a random position or random direction desired by a user by using the three-dimensional image of the object.

Recently, due to developments in semiconductor and data processing technologies, X-ray imaging has been rapidly replaced with Digital Radiography (DR) using a digital detector, and imaging methods have been variously improved.

FIG. 1 is a view illustrating an X-ray panorama image mainly utilized in the dental field. The X-ray panorama image displays teeth arrangement spread in a penetration image according to a predetermined trace of a dental arc. Accordingly, an entire teeth arrangement may be easily understood as a single image, and thus the X-ray panorama image is used as the most familiar standard image by dentists. However, an accuracy level of length information of a general panorama image is low, and there is a limitation of a projection image, such as an overlap of teeth and blurring by the cervical spine. FIG. 2 is a view illustrating an example, commonly used in the dental field, of an X-ray computerized tomography (CT) image for a head. An object to be imaged, for example, an entire head to be imaged, is located in a field of view (FOV), and a penetration image is obtained in each of imaging positions by performing X-ray imaging. Further, a three-dimensional image is produced by performing image processing, and a tomogram at a selected position from the three-dimensional image is produced and displayed. Accordingly, the three-dimensional image for the entire FOV and tomograms according to a position and a direction desired by a user may be accurately and clearly displayed. Due to this, the three-dimensional image is utilized when high-degree accuracy is required, for example, an implant procedure. However, a general three-dimensional X-ray image device is problematic in that the amount of radiation exposed to a patient is relatively high and an expensive large area detector is required.

When imaging for producing the three-dimensional X-ray image according to the related art, it is necessary that an entire object to be imaged is located within the FOV. Thus, the large area detector compared with a detector for imaging the X-ray panorama is required. For example, a case, in which a CT image is obtained in a state of positioning the object within the FOV of a first height t1 and a first width w1 by using the X-rays formed in a cone beam shape mainly used in a dental field, is described below. In this case, when a second height t2 of the detector is a value obtained by multiplying magnification by the first height t1 or more (t2 ≥ a value obtained by multiplying magnification by t1) and a second width w2 of the detector is a value obtained by multiplying magnification by the first width w1 or more (w2 ≥ a value obtained by multiplying magnification by w1), the X-rays for an entire area, which have penetrated the FOV, may be received.

Meanwhile, if a vertical shaft longitudinally parallel to the FOV is the same as rotary shafts of an X-ray source and the detector and if the X-ray source and the detector are rotated 360 degrees based on the rotary shafts, a relatively small detector may be used in case of a half beam method, capable of decreasing the second width w2 of the detector to a value obtained by multiplying the maximum magnification by w1 divided by 2, is used. However, under any methods, at the time of X-ray imaging for producing a three-dimensional image, the area of the detector producing a three-dimensional image should be much larger than the area of the detector for X-ray panorama imaging. When it is required to obtain the X-ray panorama image and the three-dimensional image that have equal heights to a height of the object, an X-ray panorama image detector is formed in a slit shape having a width ranging from only 5 to 10 mm. Meanwhile, an X-ray detector for producing a three-dimensional image is formed in a square shape whose width is approximate to a height thereof. Generally, since a price of a detector is considerably increased depending on an area thereof, it is not possible for an X-ray device for producing a three-dimensional image to avoid cost increase caused by a large area detector, thereby increasing in equipment cost. Further, when an area of a sensor is increased, the weight of equipment is increased. Thus, it is problematic in that a size of equipment should be larger because a focal spot to detector distance (FDD) is increased as well so that the FOV can be ensured.

DISCLOSURE

Technical Problem

Accordingly, the present invention is made to solve the above problems, and the present invention is intended to propose an X-ray imaging device that is accurate and intuitive for target areas of an object to be imaged by using a detector having a small area, using a low dose of irradiated X-rays, and having short operation time, compared to an existing X-ray device producing a three-dimensional image.

Technical Solution

In order to achieve the above object, according to one aspect of the present invention, there is provided an X-ray imaging device, the device including: an X-ray radiation unit for radiating X-rays to predetermined target areas of an object to be imaged in respective imaging positions; an X-ray sensing unit for receiving the X-rays that have passed through the target areas in the respective imaging positions, and forming X-ray projection data of the target areas; a movement unit for arranging the X-ray radiation unit and the X-ray sensing unit to allow the X-ray radiation unit and the X-ray sensing unit to face each other with the object located therebetween in each of the imaging positions by rotating at least one of the X-ray radiation unit and the X-ray sensing unit based on a variable rotary shaft, during a single imaging operation in which image information is obtained by radiating the X-rays to all the target areas of the object; a position information provision unit for providing position information of the target areas in the respective imaging positions, position information of the variable rotary shaft, and position information of the X-ray radiation unit and the X-ray sensing unit, which are preset so that at least a part of a first target area in a previous imaging position is irradiated in an overlapping manner with the X-rays radiated to a second target area in a next imaging position, during the single imaging operation; a control unit for controlling the X-ray radiation unit, the X-ray sensing unit, and the movement unit based on the position information of the target areas in the respective imaging positions and the position information of the X-ray radiation unit and the X-ray sensing unit; and an image processing unit for producing a three-dimensional image of the object from the projection data obtained during the single imaging operation.

Advantageous Effects

The present invention is intended to provide an X-ray imaging device, the device receiving multidirectional X-rays that have passed an object to be imaged by using a detector having a small width, and the device obtaining projection data for producing a three-dimensional image of the object. Accordingly, the device can display a tomogram and a three-dimensional image that have high level accuracy for a desired area by using a detector having a small area, using low dose of irradiated X-rays, and having short imaging time, compared to existing X-ray Computerized Tomography (CT) imaging.

Furthermore, the present invention can provide an accurate and intuitive image for a position and a direction desired by a user, such as a panorama image, by using a tomogram and a three-dimensional image for a part desired to be analyzed by a user. Further, since problems of a projection image, such as overlapping teeth and blurring by the cervical spine, do not exist in the image according to the present invention, it is advantageous in that the device can be widely used.

Furthermore, a digital X-ray panorama detector according to the related art is configured such that an X-ray film thereof is replaced only. However, in the present invention, a three-dimensional panorama digital image can be provided.

BEST MODE

Figure 1:
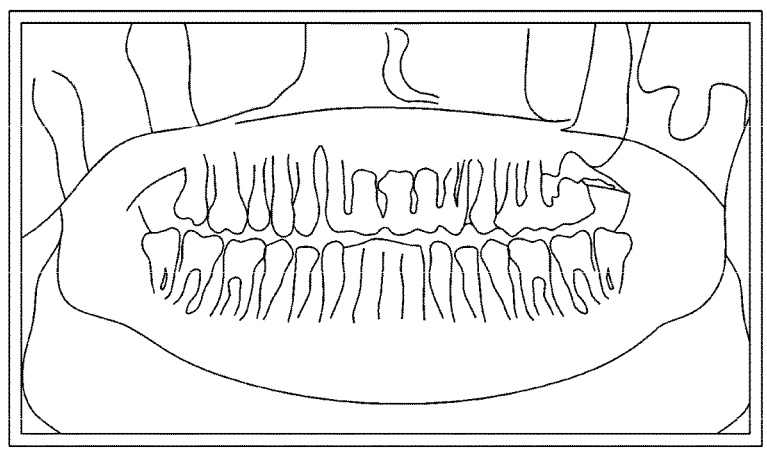
FIG. 1 is a view illustrating an X-ray panorama image for dental use according to the related art.
Figure 2:
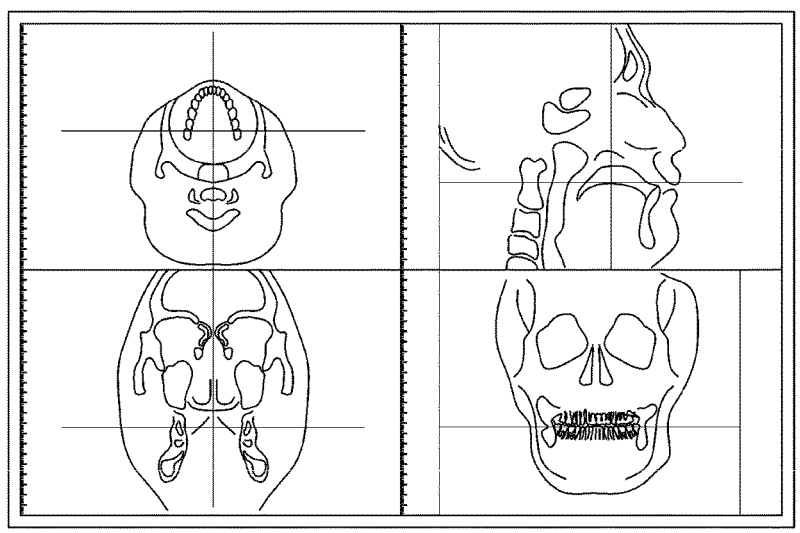
FIG. 2 is a view illustrating a Computerized Tomography (CT) image for dental use according to the related art.

An X-ray imaging device according to the present invention moves along a variable rotary shaft and performs X-ray imaging. Further, the X-ray imaging device produces a three-dimensional image of an object to be imaged by using a detector having a small width that only obtains projection image information of target areas as parts of the object in respective imaging positions. The X-ray imaging device according to the present invention includes: an X-ray radiation unit for radiating X-rays to predetermined target areas of the object in the respective imaging positions; an X-ray sensing unit for receiving the X-rays that have passed through the target areas in the respective imaging positions, and forming X-ray projection data of the target areas; a movement unit for arranging the X-ray radiation unit and the X-ray sensing unit to allow the X-ray radiation unit and the X-ray sensing unit to face each other with the object located therebetween in each of the imaging positions by rotating at least one of the X-ray radiation unit and the X-ray sensing unit based on the variable rotary shaft, during a single imaging operation in which image information is obtained by radiating the X-rays to all the target areas of the object; a position information provision unit for providing position information of the target areas in the respective imaging positions, position information of the variable rotary shaft, and position information of the X-ray radiation unit and the X-ray sensing unit, which are preset so that at least a part of a first target area in a previous imaging position is irradiated in an overlapping manner with the X-rays radiated to a second target area in a next imaging position, during the single imaging operation; a control unit for controlling the X-ray radiation unit, the X-ray sensing unit, and the movement unit based on the position information of the target areas in the respective imaging positions and the position information of the X-ray radiation unit and the X-ray sensing unit; and an image processing unit for producing the three-dimensional image of the object from the projection data obtained during the single imaging operation. Further, a size of each of the target areas is smaller than one-half of a projected size of the object.

The device further includes a detector having an entire active area comprising a pixel array, the detector receiving the X-rays that have passed through the target areas at the entire active area, and providing the X-ray projection data as an electric signal corresponding to the X-rays that are received.

The device further includes the image processing unit for producing the three-dimensional image of the object from the projection data obtained during the single imaging operation, and a display unit for displaying the three-dimensional image of the object.

The device further includes an input unit for receiving position information of the three-dimensional image, in which the image processing unit produces a tomogram of the input position information, and the display unit displays the tomogram.

The device is for dental use, and the object is a dental arch.

The device further includes an input unit for receiving position information of a layer on the three-dimensional image of the dental arch, in which the image processing unit produces a panorama tomogram of the dental arch corresponding to the layer, and the display unit displays the panorama tomogram.

MODE FOR INVENTION

Hereinafter, embodiments of the present invention are described in detail with reference to the accompanying drawings.

Although embodiments of an X-ray imaging device for dental use according to the present invention are disclosed below for illustrative purposes, the scope of the present invention is not limited thereto. Further, those skilled in the art will easily appreciate that the scope of the present invention are applicable to all the related X-ray imaging devices with reference to descriptions below. Further, the accompanying drawings are illustrated for reference to understand the scope of the present invention, and sizes of respective components and mutual sizes between components shown in the accompanying drawings may be different from the actual sizes.

Figure 3A:
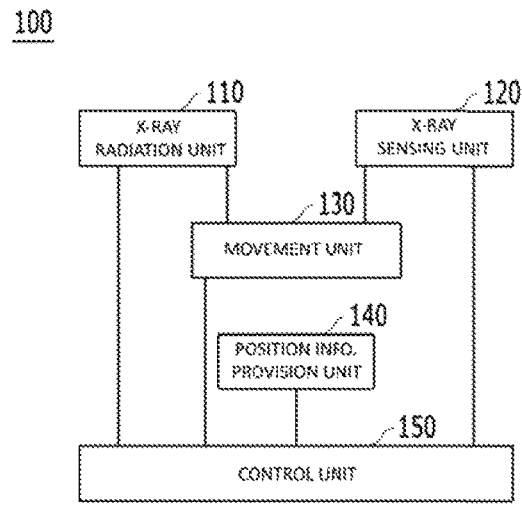
FIG. 3a, FIG. 3b and FIG. 3c are a schematic view illustrating a configuration of an X-ray imaging device according to an embodiment of the present invention.

FIG. 3a is a schematic view illustrating a configuration of an X-ray imaging device 100 according to an embodiment of the present invention. The X-ray imaging device 100 includes an X-ray radiation unit 110, an X-ray sensing unit 120, a movement unit 130, a position information provision unit 140, and a control unit 150.

The X-ray radiation unit 110 may include a controller, such as a collimator, for controlling radiation angles and radiation areas of X-rays, and radiates X-rays to predetermined target areas of an object to be imaged in respective imaging positions. It is desirable that a size of each of the target areas is smaller than one-half of a projected size of the object. In the X-ray imaging device for dental use, the object is a dental arch, and the target areas may be parts of the dental arch. Preferably, the entire field of view (overlapping FOVs in all the respective imaging positions) of the X-ray imaging device for dental use according to the embodiment of the present invention may be designed in a dental arch shape, but is not limited thereto.

Figure 4A:
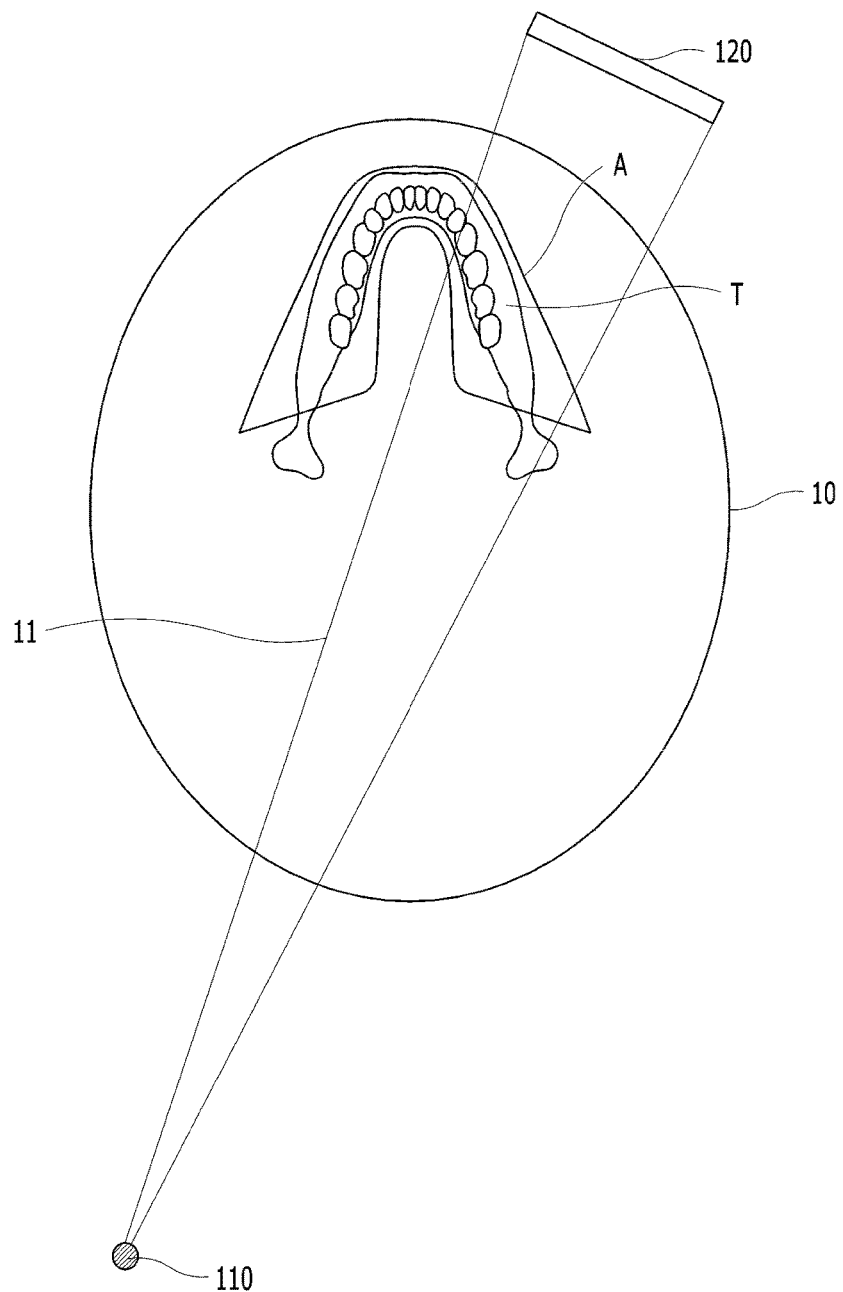
FIG. 4a is a schematic view illustrating an example of imaging for producing an X-ray image according to the embodiment of the present invention.
Figure 4B:
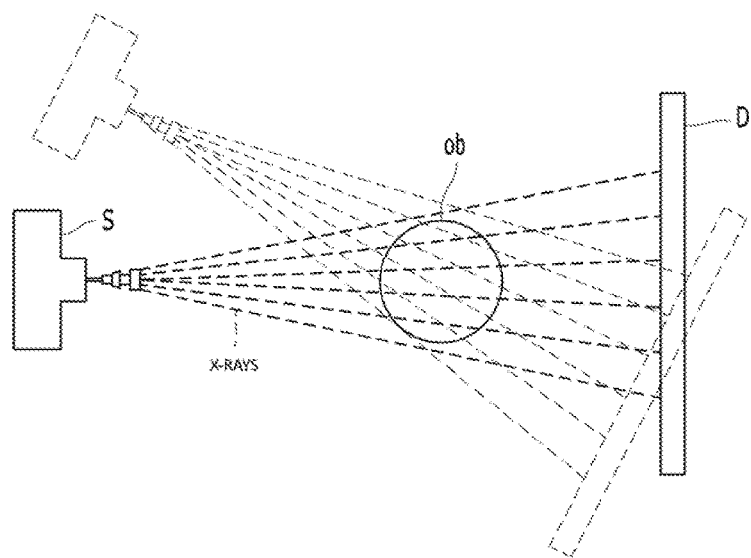
FIG. 4b is a schematic view illustrating an example of imaging for producing a three-dimensional X-ray image according to the related art.

Referring to FIG. 4a, the X-ray sensing unit 120 and the X-ray radiation unit 110 are faced with each other while an object to be imaged A is located therebetween, and X-ray projection data is formed by receiving X-rays that have passed through target areas T in respective imaging positions. The X-ray sensing unit 120 includes a detector having an entire active area including a pixel array, the detector receiving the X-rays that have passed through the target areas T at the entire active area, and providing the X-ray projection data, which is formed in a pixel array data shape, as an electric signal corresponding to the X-rays that are received. According to the present invention, since it is not required to detect the X-rays radiated to the entire object A in each of the imaging positions, a width of the detector is less than a value obtained by multiplying a radius of a minimal circle including a part of the object by magnification, which is sufficient. In the X-ray imaging device for dental use according to the embodiment of the present invention, the object A is the dental arch A located in patient's head 10, and when it is required to obtain a three-dimensional X-ray image of the dental arch A, a width of the detector may be smaller than a value obtained by multiplying a radius of a minimal circle including the target areas of the dental arch A by magnification. The width of the detector may range from 10 mm to 50 mm, and preferably, may be 36 mm. As shown in FIG. 4b, in an X-ray imaging device producing a three-dimensional image and tomogram according to the related art, while an X-ray radiation unit S and a detector D are rotated based on a fixed rotary shaft (not shown in the drawings) that is located therebetween and extends from a point of an object to be imaged OB, X-rays are radiated to the entire area (for example, a dental arch) of the object OB in each of the imaging positions. Thus, the X-rays, which have passed through the object OB, are projected on the detector D. In contrast, in the X-ray imaging device according to the present invention, referring back to the FIG. 4a, while at least one of the X-ray radiation unit 110 and the X-ray sensing unit 120 moves, X-rays are radiated from the X-ray radiation unit 110 to the target areas T other than the entire object A in the predetermined respective imaging positions, and the X-rays, which have passed through the target areas T, are projected on the detector of the X-ray sensing unit 120.

The movement unit 130 arranges the X-ray radiation unit 110 and the X-ray sensing unit 120 to allow the X-ray radiation unit and the X-ray sensing unit to face each other with the object located therebetween in each of the imaging positions by rotating at least one of the X-ray radiation unit 110 and the X-ray sensing unit 120 based on a variable rotary shaft, during a single imaging operation in which image information is obtained by radiating the X-rays to all the target areas of the object. The variable rotary shaft may be located between the X-ray radiation unit 110 and the X-ray sensing unit 120.

During the X-ray imaging operation, the X-ray radiation unit 110 and/or the X-ray sensing unit 120 perform/performs a predetermined imaging operation in a state of facing each other along a predetermined trace around the object 10 by repeatedly moving and imaging. In the embodiment of the present invention, the X-ray radiation unit 110 and the X-ray sensing unit 120 are disposed at opposite ends of a structure, such as a gantry (not shown in the drawings), in a state of facing each other, and may be rotated based on a rotary shaft located therebetween. Further, the gantry may be moved in a direction parallel to the rotary shaft, and thus heights of the X-ray radiation unit 110 and the X-ray sensing unit 120 may be adjusted. The gantry may be horizontally moved, and a movement trace of the gantry and the rotation amount of the gantry may be variously adjusted in each of the imaging positions by using the movement unit 130.

The position information provision unit 140 provides position information of the target areas in the respective imaging positions and position information of the X-ray radiation unit 110 and the X-ray sensing unit 120. The X-ray imaging device for producing a three-dimensional image according to the related art radiates the X-rays to the entire area of the object in each of the imaging positions. However, the X-ray imaging device according to the present invention radiates the X-rays to only the target areas of the object in the respective imaging positions. Thus, it is required to radiate multidirectional X-rays to all the substantial areas of the object in a path of at least any one of the X-ray radiation unit 110 and the X-ray sensing unit 120. In this case, all the substantial areas do not mean perfectly all the areas of the object, and mean the areas of the object to which the X-rays are radiated so that a desired purpose of the imaging operation is achieved.

Figure 5A:
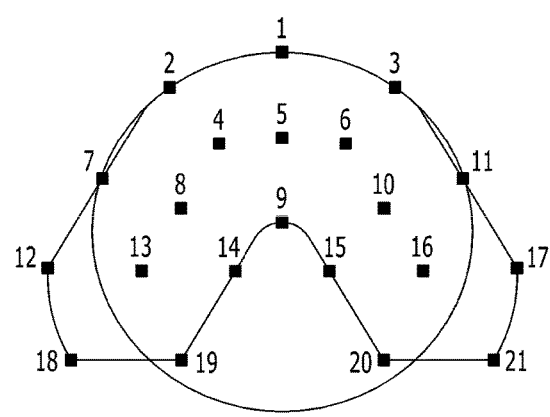
FIG. 5a is a schematic view illustrating centers of target areas corresponding to respective imaging positions according to the present invention.

In the X-ray imaging device according to the present invention, at least a part of a first target area in a previous imaging position is irradiated in an overlapping manner with the X-rays radiated to a second target area in a next imaging position. Accordingly, incidence angles of the X-rays in the respective target areas are different from each other. Further, it is not necessary that the previous imaging and the next imaging are directly adjacent to each other, and it is sufficient to radiate the multidirectional X-rays to all the substantial areas of the object during the single imaging operation. In the X-ray imaging device according to the present invention, when the multidirectional X-rays are radiated or detected, an operation of the gantry is appropriately controlled so that the X-rays exist within predetermined angle ranges in the respective target areas. FIG. 5*a* illustrates centers 1 to 21 of the target areas in the respective imaging positions, and FIG. 5*b* illustrates direction dispersion of the X-rays radiated to the centers of the respective target areas according to the completion of the single imaging operation.

Figure 5B:
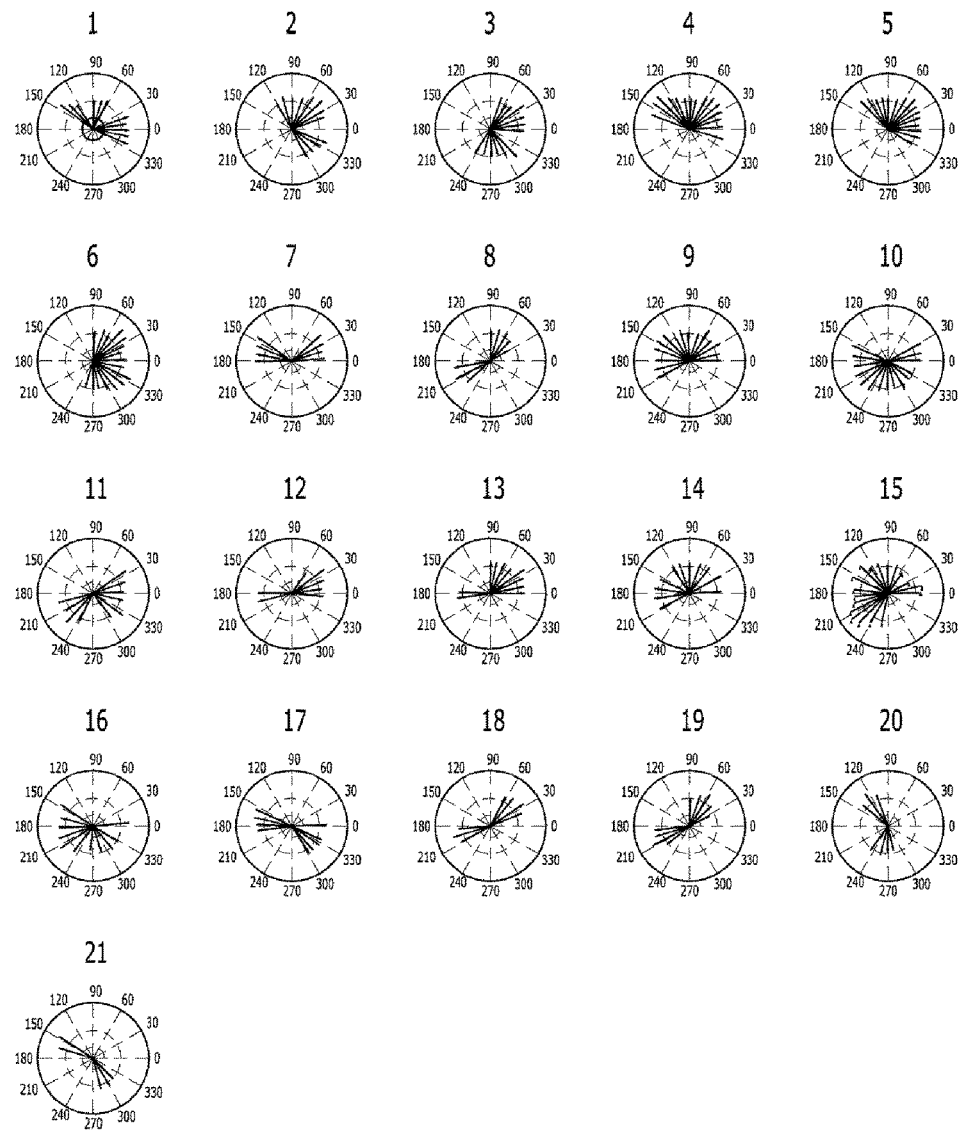
FIG. 5b a view illustrating radiation direction dispersion of X-rays radiated to each of the target areas of an object to be imaged.
Figure 5C:
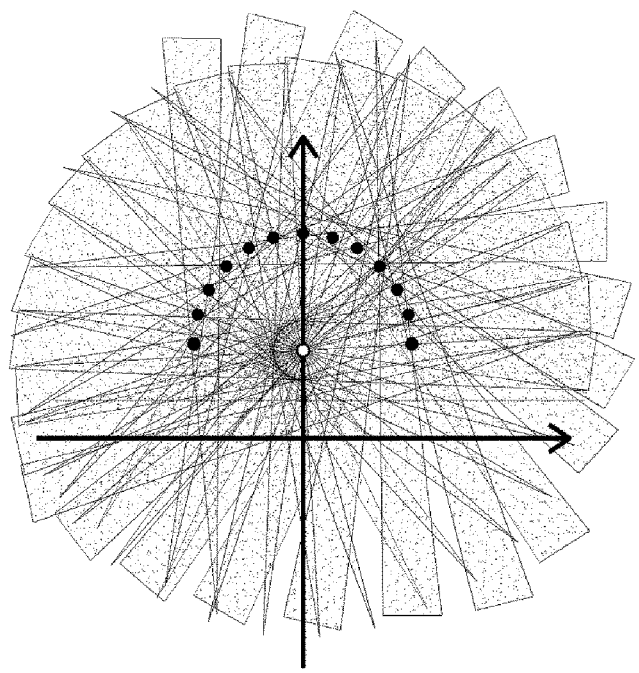
FIG. 5c is an X-ray overlapping view obtained by performing a single imaging operation.

As shown in FIG. 5*b*, the position information provision unit 140 provides the position information of the target areas in the respective imaging positions, information of the rotary shaft, and the position information of the X-ray radiation unit and the X-ray sensing unit, which are determined to radiate the multidirectional X-rays to the respective target areas, during the single imaging operation. FIG. 5*a* and FIG. 5*b* illustrate an example of the direction dispersion of the X-rays in each of the target areas. Further, when the X-ray imaging device is designed, the dispersion of the incidence angles of the X-rays of the target areas in the respective imaging positions may be appropriately controlled by using this type of example as a reference. FIG. 5*c* is an X-ray overlapping view obtained by performing the single imaging operation in such a way that the movement unit 130 is operated based on positions of the target areas in the respective imaging positions, the position information of the target areas in the respective imaging positions, which is provided beforehand in the position information provision unit 140 considering a position correlation between the X-ray radiation unit and the X-ray sensing unit, and the position information of the X-ray radiation unit and the X-ray sensing unit so that the direction dispersion of the X-rays of the respective target areas, as shown in and FIGS. 5*a* and 5*b*, can be obtained. As shown in FIG. 5*c*, in the X-ray imaging device according to the embodiment of the present invention, the multidirectional X-rays are radiated to the entire object A, i.e., all the substantial areas of the dental arch, during the single imaging operation.

The control unit 150 controls the X-ray radiation unit 110, the X-ray sensing unit 120, and the movement unit 130 based on the position information of the target areas in the respective imaging positions and the position information of the X-ray radiation unit and the X-ray sensing unit.

Figure 3B:
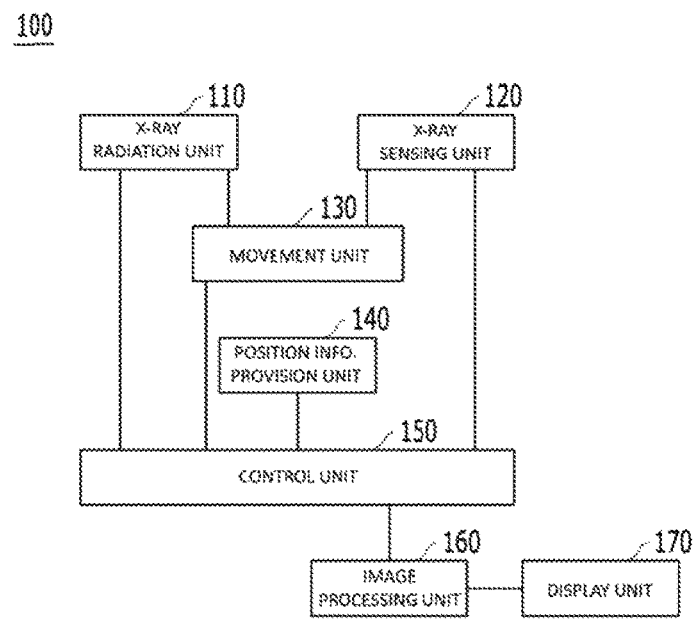

Referring to FIG. 3*b*, an X-ray imaging device according to another embodiment of the present invention further includes an image processing unit 160 producing the three-dimensional image of the object from the X-ray projection data obtained during the single imaging operation, and a display unit 170 displaying the three-dimensional image of the object. The image processing unit 160 and the display unit 170 may be realized by using a desktop or laptop computer.

The image processing unit 160 appropriately processes projection image information of each of the target areas by performing image processing, and produces three-dimensional image data. The image processing unit 160 forms first voxel data for the respective target areas or the entire object by using pixel array data corresponding to all the imaging positions, calculates a voxel correction value based on information of the number of X-ray radiations and an X-ray radiation direction in each voxel based on the X-ray radiation direction in each of the imaging positions, and forms the three-dimensional image of the entire object, i.e., second voxel data, by applying the calculated voxel correction value to the first voxel data. For this purpose, the position information of the target areas in the respective imaging positions and the position information of the X-ray radiation unit and the X-ray sensing unit, which are stored in the position information provision unit 140, may be stored in or shared with the image processing unit 160 as well.

Figure 6:
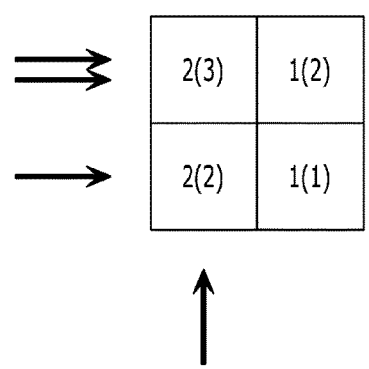
FIG. 6 is an exemplary view illustrating a method of compensating an overlapping view considering directions according to the embodiment of the present invention.
Figure 7:
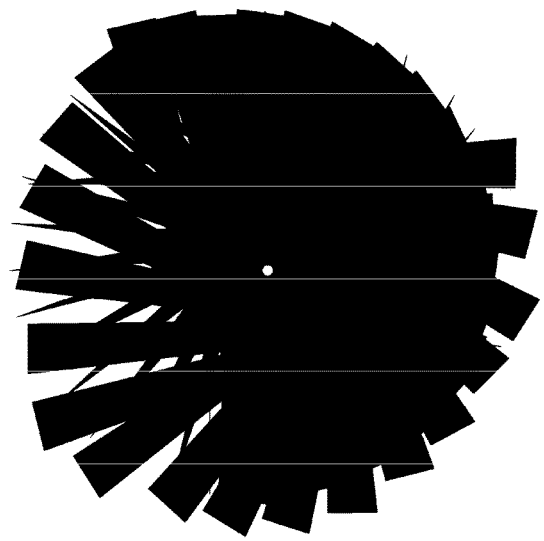
FIG. 7 is a view illustrating a completed example of X-ray overlapping section compensation of the X-ray imaging device according to the present invention.

The voxel correction value may be determined by using the overlapping view considering the number of X-rays and a direction of X-rays, which pass through the voxel. In FIG. 6 schematically illustrating the voxel as a two-dimensional view, numbers in parentheses mean the number of X-rays passing through each voxel, and numbers outside parentheses mean the number of X-rays on which weighting is reflected. Further, direction weighting is taken into account without making a sensitivity map in such a way that a value of the X-rays passing through each voxel is unconditionally set as 1 so as to make the weighting having a desired size. Further, a part, in which two X-rays are horizontally inserted, has the weighting valued at 0.5 in each of the part. In another example, the voxel correction value may be reconstructed twice by making filtered back projection (FBP) considering a direction and the sensitivity map considering a direction. However, when the weighting considering a direction is reflected, the voxel correction value may be reconstructed at once. In the image processing unit 160, when overlapping portions shown in FIG. 5*c* reflect the weighting of data that is not compensated and are reconstructed by using an FBP algorithm including back projection (BP), a result shown in FIG. 7 may be obtained by compensating the overlapping portions of the X-rays depending on X-ray directions.

Figure 3C:
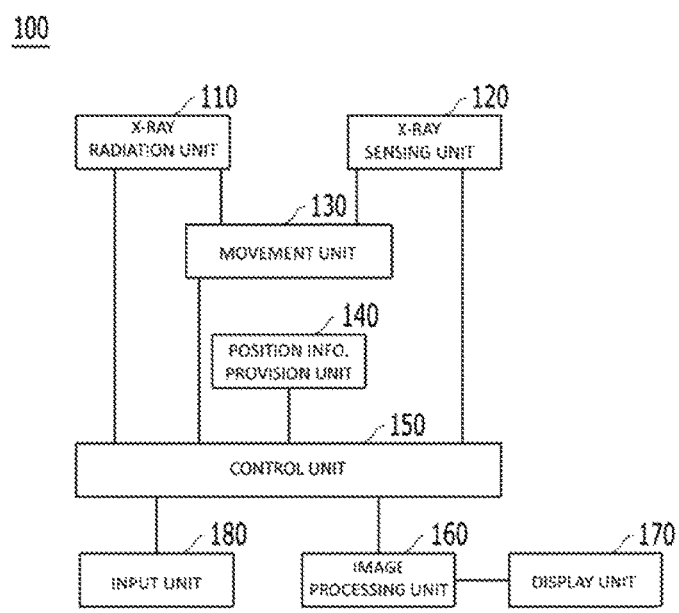

Referring to FIG. 3*c*, the X-ray imaging device further includes an input unit for receiving position information of the three-dimensional image. The input unit may be realized as a variety of forms, such as a mouse, keyboard, or touch screen. Further, the image processing unit 160 produces a tomogram of the input position information from the three-dimensional image data, and the display unit 170 displays the tomogram. The three-dimensional imaging device is an X-ray imaging device for dental use, and the object is a dental arch. Further, the input unit 180 may receive position information of a layer on the three-dimensional image of the dental arch. In this case, the image processing unit produces a panorama tomogram of the dental arch corresponding to the layer, and the display unit displays the panorama tomogram.

Figure 8:
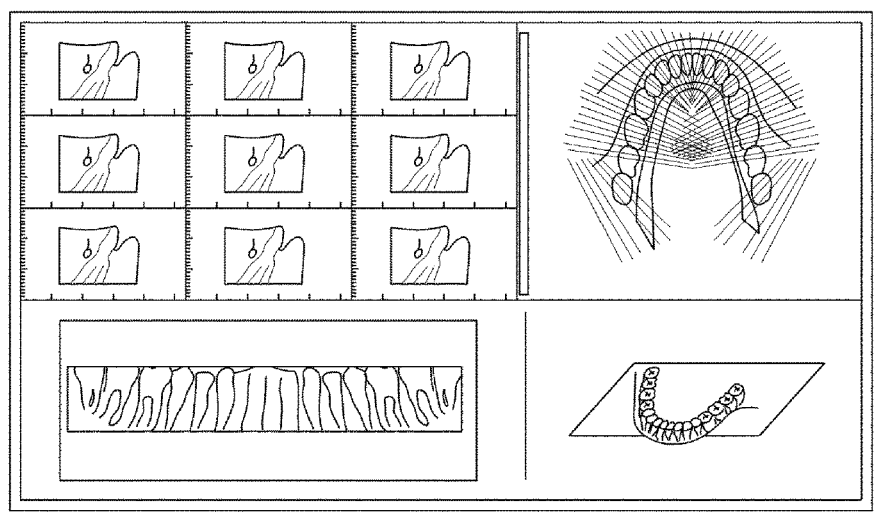
FIG. 8 is an exemplary view illustrating display of an image processing unit in an X-ray image production method according to the present invention.

FIG. 8 is a view illustrating an example of display screen displayed to a user via the display unit of the X-ray imaging device according to the present invention. The display unit may display the object, such as the three-dimensional image of the dental arch (a lower right end), i.e., a three-dimensional panorama image, a variety of tomograms according to a position and a direction randomly desired by a user (an upper left end), an axial tomogram (an upper right end) showing an entire trace of the dental arch based on a predetermined position by a user, and the panorama section (an lower left end) vertical about the predetermined trace by a user in the axial tomogram. The panorama section is the most familiar standard image used by dentists, and since the panorama section is converted from a three-dimensional image into a tomogram, length information is very accurate. Further, there is no limitation of a projection image, such as overlapping teeth and blurring by a cervical spine. Thus, a utilization scope is very wide.

Although the embodiments of the present invention have been disclosed for illustrative purposes with reference to the drawings, the present invention, however, is not limited thereto. Those skilled in the art will appreciate that the present invention can be embodied in many alternate forms and also appreciate that various modifications, additions and substitutions are possible, without departing from the scope of the invention as disclosed in the accompanying claims and drawings. Accordingly, the present invention is intended to cover not only the embodiments, but also various alternatives, modifications, equivalents and other embodiments. In addition, the scope of the present invention is defined by the accompanying claims and their equivalents if appropriate.

INDUSTRIAL APPLICABILITY

The present invention is intended to provide an X-ray imaging device, the device receiving multidirectional X-rays that have passed an object to be imaged by using a detector having a small width, and the device obtaining projection data for producing a three-dimensional image of the object. Accordingly, the device can display a tomogram and a three-dimensional image that have high level accuracy for a desired area by using a detector having a small area, using low doses of irradiated X-rays, and having short imaging time, compared to an existing X-ray Computerized Tomography (CT) imaging.

The invention claimed is:

1. An X-ray imaging device, the device comprising:
an X-ray radiation unit configured to radiate X-rays to predetermined target areas of an object to be imaged in respective imaging positions;
an X-ray sensing unit configured to receive the X-rays that have passed through the predetermined target areas in the respective imaging positions, and forming X-ray projection data of the target areas;
a movement unit configured to arrange the X-ray radiation unit and the X-ray sensing unit to allow the X-ray radiation unit and the X-ray sensing unit to face each other with the object located therebetween in each of the imaging positions by rotating at least one of the X-ray radiation unit and the X-ray sensing unit based on a variable rotary shaft, during a single imaging operation wherein an image information is obtained by radiating the X-rays to all the target areas of the object;
a position information provision unit configured to provide a position information for a plurality of centers of the target areas in the respective imaging positions, a position information of the variable rotary shaft, and a position information of the X-ray radiation unit and the X-ray sensing unit, wherein the X-rays are raditated to the plurality of center of the target areas and at least a part of a first target area in a previous imaging position is irradiated in an overlapping manner with the X-rays radiated to a second target area in a next imaging position, and wherein the X-rays exist within predetermined angle ranges in the respective target areas, during the single imaging operation;
a control unit configured to control the X-ray radiation unit, the X-ray sensing unit, and the movement unit based on the position information of the target areas in the respective imaging positions and the position information of the X-ray radiation unit and the X-ray sensing unit; and
an image processing unit configured to form a three-dimensional image of the object from the projection data obtained during the single imaging operation.

2. The device of claim 1, wherein a size of each of the target areas is smaller than one-half of a projected size of the object.

3. The device of claim 2, further comprising:
a detector configured to receive X-rays by an entire active area of a pixel array, and provide the projection data as an electric signal corresponding to the X-rays.

4. The device of claim 3, wherein the image processing unit is configured to produce the three-dimensional image of the object from the projection data obtained during the single imaging operation; and
wherein the device further comprises a display unit configured to display the three-dimensional image of the object.

5. The device of claim 4, further comprising:
an input unit configured to receive a position information of the three-dimensional image, wherein the image processing unit is configured to produce a tomogram of the input position information, and the display unit is configured to display the tomogram.

6. The device of claim 4, wherein the device is for dental use, and the object is a dental arch.

7. The device of claim 6, further comprising:
an input unit configured to receive a position information of a layer on the three-dimensional image of the dental arch, and wherein the image processing unit is configured to produce a panorama tomogram of the dental arch corresponding to the layer, and the display unit displays the panorama tomogram.

8. The device of claim 1, wherein the image processing unit is configured:
to form a first voxel data for a plurality of voxels corresponding to the object by using a pixel array data corresponding to all the imaging positions,
to calculate a voxel correction value based on information of a number of X-ray radiations and an X-ray radiation direction in each voxel of the plurality of voxels based on the X-ray radiation direction in each of the imaging positions,
to form a second voxel data by applying the calculated voxel correction value to the first voxel data, and
to produce the three-dimensional image of the object by using the second voxel data.

9. An X-ray imaging device, the device comprising:

an X-ray radiation unit configured to radiate X-rays to predetermined target areas of an object to be imaged in respective imaging positions;

an X-ray sensing unit configured to receive the X-rays that have passed through the predetermined target areas in the respective imaging positions, and forming X-ray projection data of the target areas, and wherein the X-ray sensing unit includes a detector having a width less than a value obtained by multiplying a radius of a minimal circle including a part of the object of magnification;

a movement unit configured to arrange the X-ray radiation unit and the X-ray sensing unit to allow the X-ray radiation unit and the X-ray sensing unit to face each other with the object located therebetween in each of the imaging positions by rotating at least one of the X-ray radiation unit and the X-ray sensing unit based on a variable rotary shaft, during a single imaging operation wherein an image information is obtained by radiating the X-rays to all the target areas of the object;

a position information provision unit configured to provide a position information for a plurality of centers of the target areas in the respective imaging positions, a position information of the variable rotary shaft, and a position information of the X-ray radiation unit and the X-ray sensing unit, wherein the X-rays are raditated to the plurality of center of the target areas and at least a part of a first target area in a previous imaging position is irradiated in an overlapping manner with the X-rays radiated to a second target area in a next imaging position, and wherein the X-rays exist within predetermined angle ranges in the respective target areas, during the single imaging operation;

a control unit configured to control the X-ray radiation unit, the X-ray sensing unit, and the movement unit based on the position information of the target areas in the respective imaging positions and the position information of the X-ray radiation unit and the X-ray sensing unit; and an image processing unit configured to form a three-dimensional image of the object from the projection data obtained during the single imaging operation.

* * * * *